US011735310B2

(12) United States Patent
 Neumann

(10) Patent No.: US 11,735,310 B2
(45) Date of Patent: Aug. 22, 2023

(54) SYSTEMS AND METHODS FOR GENERATING A PARASITIC INFECTION NUTRITION PROGRAM

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 48 days.

(21) Appl. No.: 17/136,265

(22) Filed: Dec. 29, 2020

(65) Prior Publication Data

US 2022/0208343 A1    Jun. 30, 2022

(51) Int. Cl.

| | | |
|---|---|---|
| *G16H 20/60* | (2018.01) | |
| *G16H 10/60* | (2018.01) | |
| *G16H 70/60* | (2018.01) | |
| *G16H 50/20* | (2018.01) | |
| *G06N 20/00* | (2019.01) | |
| *A61B 5/11* | (2006.01) | |
| *G01S 19/01* | (2010.01) | |

(Continued)

(52) U.S. Cl.
CPC ............ *G16H 20/60* (2018.01); *A61B 5/1112* (2013.01); *G01S 19/01* (2013.01); *G06N 20/00* (2019.01); *G16H 10/60* (2018.01); *G16H 50/20* (2018.01); *G16H 50/80* (2018.01); *G16H 70/60* (2018.01); *A61B 5/4833* (2013.01)

(58) Field of Classification Search
None
See application file for complete search history.

(56) References Cited

U.S. PATENT DOCUMENTS

| | | |
|---|---|---|
| 7,054,758 B2 | 5/2006 | Gill-Garrison |
| 7,074,183 B2 | 7/2006 | Castellanos |

(Continued)

FOREIGN PATENT DOCUMENTS

| | | |
|---|---|---|
| RU | 2691145 C2 | 6/2019 |
| WO | 2014015378 | 1/2014 |

(Continued)

OTHER PUBLICATIONS

Title:Blastocystis: how do specific diets and human gut microbiota affect its development and pathogenicity? Date: By: Lepczynska.

*Primary Examiner* — Shahid Merchant
*Assistant Examiner* — Andrew E Lee
(74) *Attorney, Agent, or Firm* — Caldwell Intellectual Property Law

(57) ABSTRACT

A system for generating a parasitic infection nutrition program including a computing device configured to receive at least a parasitic biomarker, generate a parasitic disease assessment referring to a first parasitic infection as a function of the at least a parasitic biomarker, determine a current position of the user, identify, using the current position and the parasitic disease assessment, a parasitic infection intervention, receive a geophysical indicator relating to the user, identify, using the geophysical indicator, a parasitic prevention strategy regarding a second parasitic infection, and generate a parasitic infection nutrition program, using the parasitic infection intervention and the parasitic prevention strategy.

20 Claims, 8 Drawing Sheets

(51) Int. Cl.
*G16H 50/80* (2018.01)
*A61B 5/00* (2006.01)

(56) References Cited

U.S. PATENT DOCUMENTS

| | | | |
|---|---|---|---|
| 7,970,620 B2 | 6/2011 | Brown | |
| 8,000,982 B2 | 8/2011 | Kane | |
| 8,226,414 B2 | 7/2012 | Bodin | |
| 8,560,336 B2 | 10/2013 | Schwarzberg | |
| 8,684,922 B2 | 4/2014 | Tran | |
| 10,373,522 B2 | 8/2019 | Byron | |
| 11,056,242 B1* | 7/2021 | Jain | G16H 50/70 |
| 2002/0046060 A1 | 4/2002 | Hoskyns | |
| 2006/0074279 A1 | 4/2006 | Brover | |
| 2006/0199155 A1 | 9/2006 | Mosher | |
| 2008/0275912 A1 | 11/2008 | Roberts | |
| 2010/0070455 A1 | 3/2010 | Halperin | |
| 2010/0136508 A1 | 6/2010 | Zekhtser | |
| 2011/0093249 A1* | 4/2011 | Holmes | G16H 50/70 |
| | | | 703/6 |
| 2013/0150330 A1* | 6/2013 | Pogany | A61K 31/675 |
| | | | 514/82 |
| 2013/0318027 A1* | 11/2013 | Almogy | G16H 50/80 |
| | | | 706/52 |
| 2014/0220163 A1 | 8/2014 | Soleimani Babadi | |
| 2015/0161355 A1 | 6/2015 | Karra | |
| 2015/0297632 A1* | 10/2015 | Auclair | A61K 45/06 |
| | | | 424/195.16 |
| 2015/0356885 A1 | 12/2015 | Chen | |
| 2016/0008419 A1* | 1/2016 | Chen | A61K 31/11 |
| | | | 514/4.4 |
| 2016/0225284 A1 | 8/2016 | Schoen | |
| 2017/0002432 A1* | 1/2017 | Apte | C12Q 1/689 |
| 2018/0308389 A1 | 10/2018 | Moser | |
| 2018/0374386 A1* | 12/2018 | Benefield | A63B 24/0059 |
| 2019/0074080 A1 | 3/2019 | Appelbaum | |
| 2019/0221303 A1 | 7/2019 | Bennett | |
| 2019/0251861 A1 | 8/2019 | Wolf | |
| 2020/0024564 A1* | 1/2020 | Ezra | A61B 5/1468 |
| 2020/0138362 A1 | 5/2020 | Koumpan | |
| 2020/0294680 A1* | 9/2020 | Gupta | G06N 7/005 |
| 2020/0357516 A1* | 11/2020 | Kirby | G06K 9/6267 |
| 2021/0330253 A1* | 10/2021 | Wright | A61B 5/0022 |

FOREIGN PATENT DOCUMENTS

| | | |
|---|---|---|
| WO | 2019054737 | 3/2019 |
| WO | 2019110412 | 6/2019 |
| WO | 2019229753 | 12/2019 |

* cited by examiner

SYSTEMS AND METHODS FOR GENERATING A PARASITIC INFECTION NUTRITION PROGRAM

FIELD OF THE INVENTION

The present invention generally relates to the field of nutrient calculation for parasitic infection. In particular, the present invention is directed to systems and methods for generating a parasitic infection nutrition program.

BACKGROUND

Currently approximately one third of the world is at imminent risk for parasitic infection or currently harbors parasitic infection. Addressing parasitic infection is typically focused on diagnostic procedures focused on addressing underlying symptomology.

SUMMARY OF THE DISCLOSURE

In an aspect, a system for generating a parasitic infection nutrition program including a computing device configured to receive at least a parasitic biomarker, generate a parasitic disease assessment referring to a first parasitic infection as a function of the at least a parasitic biomarker, determine a current position of the user, identify, using the current position and the parasitic disease assessment, a parasitic infection intervention, receive a geophysical indicator relating to the user, identify, using the geophysical indicator, a parasitic prevention strategy regarding a second parasitic infection, and generate a parasitic infection nutrition program, using the parasitic infection intervention and the parasitic prevention strategy.

In another aspect, a method for generating a parasitic infection nutrition program including receiving, by a computing device, at least a parasitic biomarker, generating, by the computing device. a parasitic disease assessment referring to a first parasitic infection as a function of the at least a parasitic biomarker, determining, by the computing device, a current position of the user, identifying, by the computing device, using the current position and the parasitic disease assessment, a parasitic infection intervention, receiving, by the computing device, a geophysical indicator relating to the user, identifying, by the computing device, using the geophysical indicator, a parasitic prevention strategy regarding a second parasitic infection, and generating, by the computing device, a parasitic infection nutrition program, using the parasitic infection intervention and the parasitic prevention strategy.

These and other aspects and features of non-limiting embodiments of the present invention will become apparent to those skilled in the art upon full benefit of the disclosure in its entirety of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a parasitic infection nutrition program. In an embodiment, computing device is configured to receive a parasitic biomarker from a user. Computing device may generate a machine-learning model to determine a parasitic background of a user and provide a parasitic disease assessment as a function of a classification machine-learning process. Computing device may determine a current position relating to a user and calculate a parasitic infection rate as a function of user location. Computing device may use parasitic infection rate and parasitic disease assessment to determine unique, per-user nutrient amounts for addressing any change in parasitic infection rate and current parasitic disease state. Computing device is configured to calculate changes in parasitic infection rate between a user current position and a geophysical indicator. Computing device may use machine-learning to derive algorithms to automatedly calculate adjusted nutrient amounts and nutrition elements as a function of changes in parasitic infection rates and regional cuisines.

Figure 1:
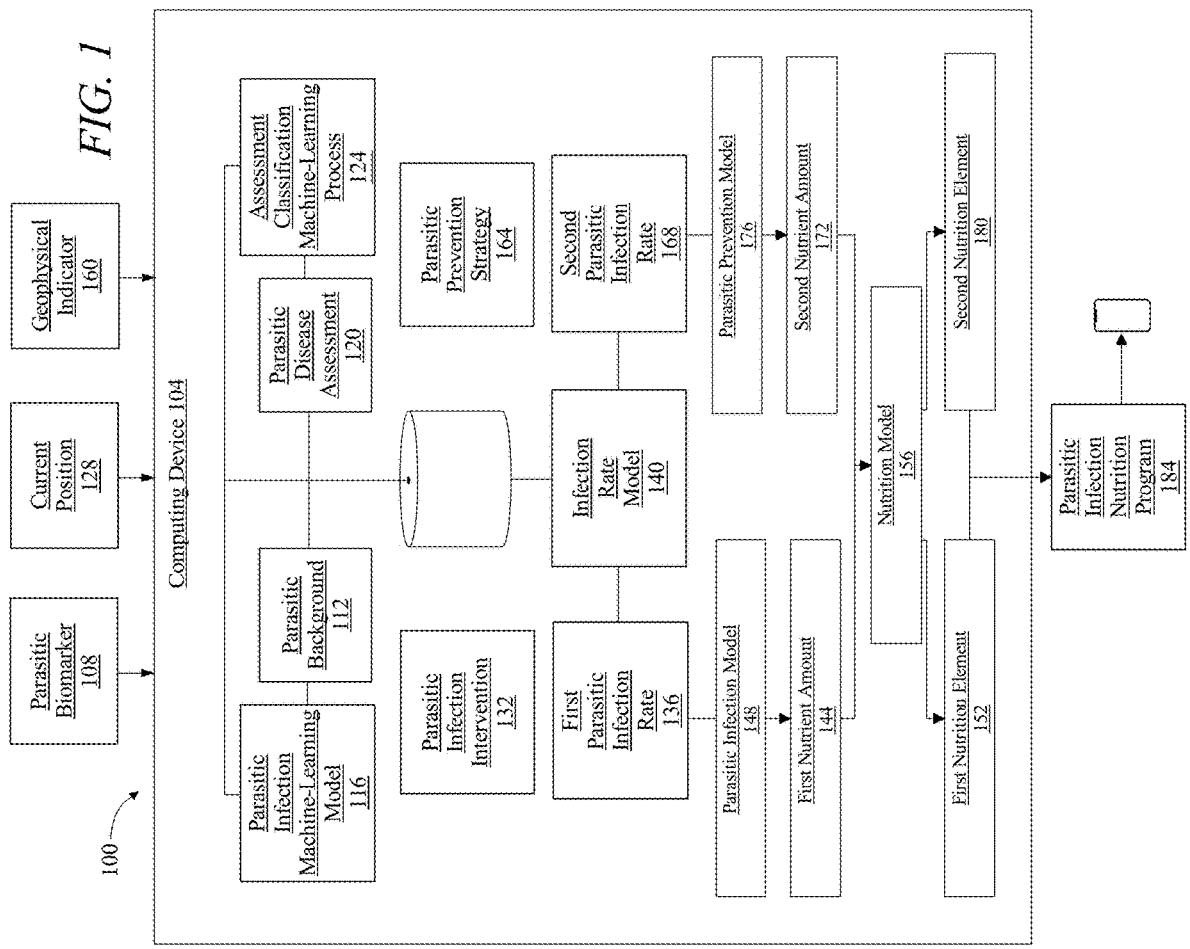
FIG. 1 is a block diagram illustrating a system for generating a parasitic infection nutrition program.

Referring now to FIG. 1, an exemplary embodiment of a system 100 for generating a microbiome balance plan for prevention of bacterial infection is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software and the like) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, computing device is configured to receive at least a parasitic biomarker. A "parasitic biomarker," as used in this disclosure, is a biological and/or chemical biomarker and/or process that originates from the user and is indicative of a relationship between the body and a parasite. A "parasite," as used in this disclosure, is any microorganism that resides on or within a user by way of a parasitic-symbiosis relationship. A parasite may include symbiotic microorganisms that present health issues in humans including malaria, *Giardia, toxoplasma, trichomonas*, threadworm, hookworm, lice, scabies, tapeworm, among other types of parasites, that may reside in biofluids, tissues, on the skin, epithelia of organs, cavities of the body, and the like Parasites may include a variety of protozoa species and subspecies (spp.), such as *Giardia lamblia, Toxoplasma gondii, Trichomonas vaginalis, Entamoeba histolytica, Plasmodium* spp., *Schistosoma mansoni, Trypanosoma* spp., *Leishmania* spp., among many others. Parasites may include a variety of helminth (worm) species and subspecies, such as *Ascaris lumbricoides, Necator americanus, Wuchereria bancrofti, Taenia solium, Onchocerca volvulus, Enterobius vermicularis*, among many others. Parasites may include a variety of trematodes (flukes) such as *Fasciola hepatica*, Dircrocoelium dentriticum, among many others. For instance and without limitation, human parasitic infection may include microorganisms that reside on or within the skin, mammary glands, placenta, seminal fluid, uterus, ovarian follicles, lung, saliva, oral mucosa, conjunctiva, biliary tract, gastrointestinal tract, and within the tissues.

Continuing in reference to FIG. 1, parasitic biomarker 108 may include analysis of molecules from a biological extraction of a user. A "biological extraction," as used in this disclosure, is a physical sample originating from a user and its analysis, such as a stool sample, blood draw, saliva swab, DNA sequencing, and the like. Parasitic biomarker 108 may include measurements of the presence of parasitic microorganisms, such as culturing results relating to microorganisms, biochemical tests for detecting the presence of parasites, microscopy searching for the presence of eggs, protozoa, worms, among other data for the presence of parasites. Parasitic biomarker 108 may include diagnostic results such as metabolic profiling, genetic sequence such as using targeted PCR probe-based profiling of biological extraction sample, biochip, microarray, test strip, and/or other sensor-based parasite profiling methods, including immobilizing macromolecules to a surface for detecting parasite from a sample. Receiving the at least a parasitic biomarker 108 may include receiving a result of one or more tests relating to the user and/or analysis of one or more biological extraction tests, for instance a fecal smear using the Kato-Katz technique. Such data may be received and/or identified as a biological extraction of a user, which may include analysis of a physical sample of a user, without limitation and as described in U.S. Nonprovisional application Ser. No. 16/886,647, filed May 28, 2020, and entitled, "METHODS AND SYSTEMS FOR DETERMINING A PLURALITY OF BIOLOGICAL OUTCOMES USING A PLURALITY OF DIMENSIONS OF BIOLOGICAL EXTRACTION USER DATA AND ARTIFICIAL INTELLIGENCE," the entirety of which is incorporated herein by reference.

Continuing in reference to FIG. 1, parasitic biomarker 108 may include test results of screening and/or early detection of infection, diagnostic procedures, prognostic indicators from other diagnoses, from predictors identified in a medical history, and information relating to biomolecules associated with the user such as the presence of and/or concentrations of: A-type natriuretic peptides, B-type natriuretic peptides, N-terminal pro-BNP, troponin I, TGF-B, MMP-2, TIMP-1, TIMP-2, CXCL9, CXCL10, CCL5, CCL8, IFN-y, IL-12p70, IL-1B, TNF, IL-10, CCL2, IL-17A, IL-4, IL-5, IL-6, CD4+, CD25+, TCR-gamma-sigma, CD8+, CD4+ DR+, CD8+DR+, CD14+, CD32+, TCR-alpha-beta, NEU, LYM, CD3+, CD3−, CD19±, MON, EOS, and the like. Parasitic biomarker 108 may include data relating to the presence and/or concentration of products relating from a microorganism such as toxins, metabolic waste products, eggs, larvae, and the like. Parasitic biomarker 108 may include data relating to the presence and/or concentration of products indicative of infection by a parasite, including particular blood serum proteins, complement, antibodies, T-cell activation in response to parasitic factors, among others.

Continuing in reference to FIG. 1, parasitic biomarker 108 may include results enumerating the identification of mutations in nucleic acid sequences. Parasitic biomarker 108 may include the presents of single nucleotide polymorphisms (SNPs) in genetic sequences in the user, as well as in an isolated parasite, for instance in the identification of drug resistant forms of malaria. Parasitic biomarker 108 may include epigenetic factors, such as non-heritable alterations to genetic information in the user and/or parasite. Parasitic biomarker 108 may include genetic and epigenetic factors for the user, for instance as a user may have mutations and/or SNPs in a variety of genes associated with increased and/or decreased susceptibility to infection such as chemokine receptor CCR5 polymorphism has been reported with variable resistance to systemic HIV infection in Caucasians but does not appear to play a signification role in populations of African of Asian descent. Parasitic biomarker 108 may include genetic and epigenetic factors for microbes originating from a user, for instance the presence of mutations regarding to drug-resistance.

Continuing in reference to FIG. 1, parasitic biomarker 108 may include data regarding host factors. A "host factor," as used in this disclosure, is any lifestyle and/or secondary factor that contributes to susceptibility to parasitic infection. Host factors may include gender, sex, ethnicity, age, pregnancy status, travel, immunosuppressive drugs, malignancy, and the like Host factors may include nutritional status such as the identification of chronic and acute nutritional deficiencies, digestive difficulties, metabolic disorders, food preferences, and the like. Host factors may include vacation travel, regional travel, or the like, where the user may have access to new populations, water sources, cuisine types, parasite reservoirs, and the like Continuing in reference to FIG. 1, computing device 104 may receive parasitic biomarker 108 as user input. User input may be received via a "graphical user interface," which as used is this disclosure, is a form of a user interface that allows a user to interface with an electronic device through graphical icons, audio indicators, text-based interface, typed command labels, text navigation, and the like, wherein the interface is configured to provide information to the user and accept input from the user. Graphical user interface may accept input, wherein input may include an interaction such as replying to health state questionnaire for symptomology onboarding, uploading a genetic sequencing file, hyperlinking a medical history document, or the like, via a user device. A person skilled in the art, having the benefit of the entirety of this disclosure, will be aware of various test data, biomarker data, analysis, and the like, that may be received as parasitic biomarker 108 data and how system 100 may receive such data as input.

Continuing in reference to FIG. 1, parasitic biomarker 108 may be organized into training data sets. "Training data," as used herein, is data containing correlations that a machine learning process, algorithm, and/or method may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine learning processes as described in further detail below.

Continuing in reference to FIG. 1, parasitic biomarker 108 may be used to generate training data for a machine-learning process. A "machine learning process," as used in this disclosure, is a process that automatedly uses a body of data known as "training data" and/or a "training set" to generate an algorithm (such as a collection of one or more functions, equations, and the like) that will be performed by a machine-learning module, as described in further detail below, to produce outputs given data provided as inputs; this is in contrast to a non-machine learning software programing where the commands to be executed are determined in advance by a subject and written in a programming language.

Continuing in reference to FIG. 1, parasitic biomarker 108 may be organized into training data sets and stored and/or retrieved by computing device 104, without limitation, as a relational database, a key-value retrieval database such as a NOSQL database, or any other format or structure for use as a database that a person skilled in the art may recognize as suitable upon review of the entirety of this disclosure. Parasitic biomarker 108 training data may alternatively or additionally be implemented using a distributed data storage protocol and/or data structure, such as a distributed hash table and the like. Parasitic biomarker 108 training data may include a plurality of data entries and/or records, as described above. Data entries may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries of parasitic biomarkers may be stored, retrieved, organized, and/or reflect data and/or records as used herein, as well as categories and/or populations of data consistent with this disclosure.

Continuing in reference to FIG. 1, computing device 104 is configured to retrieve a parasitic background related to the user. A "parasitic background," as used in this disclosure, is a profile that summarizes a user's current state with regard to parasitic infection as a function of at least the parasitic biomarker 108. Parasitic background 112 may include any number of current parasitic disease state determinations including 'past infections', 'anti-parasitic drugs taken', and the like. Parasitic background 112 may include the identification of parasite family, genus, species, strain, serotypes, and the like, of which a user has been previously infected, been exposed, and/or currently harboring as a function of patterns, trends, and/or data in parasitic biomarker 108. Parasitic background 112 may include data represented by strings, numerical values, mathematical expressions, functions, matrices, vectors, and the like. Parasitic background 112 may include a plurality of metrics and their relationships to a plurality of parasites as a function of the at least a parasitic biomarker 108, such as the presence of and degree of parasitic infection where user is located.

Continuing in reference to FIG. 1, parasitic background 112 may include qualitative determinations, such as binary "yes"/"no" determinations for harboring a parasitic species, nutritional deficiency, travel advisory, and the like, "normal"/"abnormal" determinations about the presence of and/or concentration of parasitic biomarkers 108, for instance as compared to a normalized threshold value of a biomarker among a subset of healthy adults. Parasitic background 112 may include mathematical representations of the current state of the infection, such as a function describing, for instance, the risk of developing parasitic infection as a function of time for a particular location. Such representations of parasitic background 112 may allow for determinations such as instantaneous infection risk, such as daily, weekly, monthly, and the like, risks.

Continuing in reference to FIG. 1, retrieving parasitic background 112 may include a process of searching for, locating, and returning parasitic background 112 data. For example, parasitic background 112 may be retrieved as documentation on a computer to be viewed or modified such as files in a directory, a database, and the like In non-limiting illustrative examples, computing device 104 may locate and download parasitic background 112 via a web browser and the Internet, receive parasitic background 112 as input via a software application and a user device, and the like Retrieving parasitic background 112 may include retrieving, by computing device 104, the parasitic background 112 from a database, as described in further detail below.

Continuing in reference to FIG. 1, retrieving the parasitic background 112 may include generating parasitic background training data using the at least a parasitic biomarker 108, training a parasitic background machine-learning model with the parasitic background training data that includes a plurality of data entries wherein each entry correlates parasitic biomarkers to a plurality of parasitic diseases, and generating the parasitic background 112 as a function of the parasitic background machine-learning model and the at least a parasitic biomarker.

Continuing in reference to FIG. 1, parasitic background training data may include any parasitic biomarker 108 data, as described above, organized into training data, as described herein. Such training data may include a plurality of data entries of biomarker levels correlated to types of parasitic infections. Training data may originate as analysis from biological extraction samples, health state questionnaires regarding symptomology, medical histories, physician assessments, lab work, and the like, from one or more users. Parasitic background training data may originate from the subject and/or multiple subjects, for instance via a questionnaire and a user interface with computing device 104 to provide medical history data, nutritional input, food intolerances, and the like Computing device 104 may receive training data for training parasitic background machine-learning model 116. Receiving such training data may include receiving whole genome sequencing, gene expression patterns, and the like, for instance as provided by a genomic sequencing entity, hospital, database, the Internet, and the like Parasitic background training data may include raw data values recorded and transmitted to computing device 104 via a wearable device such as a bioimpedance device, ECG/EKG/EEG monitor, physiological sensors, blood pressure monitor, blood sugar and volatile organic compound (VOC) monitor, and the like. Parasitic background training data may originate from an individual other than user, including for instance a physician, lab technician, nurse, dietician, and the like. It is important to note that training data for machine-learning processes, algorithms, and/or models used herein may originate from any source described for parasitic background training data.

Continuing in reference to FIG. 1, parasitic background machine-learning model 116 may include any machine-learning algorithm such as K-nearest neighbors algorithm, a lazy naïve Bayes algorithm, and the like, machine-learning process such as supervised machine-learning, unsupervised machine-learning, or method such as neural nets, deep learning, and the like, as described in further detail below. Parasitic background machine-learning model 116 may be trained to derive an algorithm, function, series of equations, or any mathematical operation, relationship, or heuristic, that can automatedly accept an input of parasitic biomarker(s) 108 and generate an output of a parasitic background 112. Parasitic background machine-learning model 116 may derive individual functions describing unique relationships observed from the parasitic background training data for each parasitic biomarker 108, wherein different relationships may emerge between users and user cohorts such as subsets of alike users, healthy users, obese users, 18-24 yrs. old, and the like. Parasitic background machine-learning model 116 may derive relationships from the training data which indicate patterns in parasitic infection rate or parasite types according to where a user resides, has traveled, studied abroad, vacationed, and the like Parasitic background 112 may include any number of parameters, numerical values, strings, functions, mathematical expressions, text, and the like. Parasitic background 112 may become increasingly more complete, and more robust, with larger sets of parasitic biomarkers 108.

Continuing in reference to FIG. 1, computing device 104 is configured to assign the parasitic background 112 to a parasitic disease assessment. A "parasitic disease assessment," as used in this disclosure, is a determination about a current parasitic disease state of the user according to a classification of the user as a function of a subset of users. Parasitic disease assessment 120 may include tissue or organ type classification, such as "skin infection", "blood infection", and the like Parasitic disease assessment 120 may include a microorganism species, identifier, or grouping such as "Malaria", "Hookworm," and the like Parasitic disease assessment 120 may include a designation about resistance, such as "impaired neutrophil-mediated resistance to co-infection", "drug-resistant malaria", and the like. Parasitic disease assessment 120 may include a designation regarding a type of bodily dysfunction that may involve a particular parasite. Parasitic disease assessment 120 may include a predictive classification, where a user does not currently have an infection but may include data that indicates a parasitic disease assessment 120 with which the user may be most closely categorized to such as an infection from imminent exposure. Parasitic background 112 may have associated with it an identifier, such as a label, that corresponds to a parasitic disease assessment 120, series of microorganism identities, and the like Continuing in reference to FIG. 1, assigning parasitic background 112 to parasitic disease assessment 120 may include classifying the parasitic background 112 to the parasitic disease assessment 120 using an assessment classification machine-learning process, and assigning the parasitic background 120 as a function of the classifying. Assessment classification machine-learning process 124 may include any machine-learning process, algorithm, and/or model performed by a machine-learning module, as described in further detail below. Assessment classification machine-learning process 124 may generate a classifier using training data. Training data may include parasitic species, parasitic biomarkers 108, and the like, correlated to data entries that may be recognized as parasitic infection categories, disease assessments, and the like. Training data may originate from any source as described above. A "classifier" may include a machine-learning model, such as a mathematical model, neural net, or program generated by a machine learning algorithm known as a "classification algorithm," as described in further detail below. Classifier 112 may provide "classification" by sorting inputs, such as the data in the parasitic background 112, into categories or bins of data, such as classifying the data into a parasitic disease assessment 120. Classifier may output the bins of data and/or labels associated therewith. In non-limiting illustrative examples, training data used for such a classifier may include a set of parasitic biomarkers 108 (as described above) as it relates to classes of parasitic infections, symptoms, stages of disease, regions of the world, nutritional deficiencies, and the like For instance, training data may include ranges of user biological extraction values as they relate to the variety of infections, wherein if a user presents a particular pattern of biomarkers, the classifier may automatedly sort that user to a disease category. Thus, assessment classification machine-learning process 124 may assign the parasitic background 120 as a function of the classifying.

Continuing in reference to FIG. 1, assessment classification machine-learning process 124 may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, a classifier may classify elements of training data to elements that characterizes a sub-population, such as a subset of parasitic biomarker 108 and/or other analyzed items and/or phenomena for which a subset of training data may be selected, for generating specified training data sets for subsequent process(es) described herein.

Continuing in reference to FIG. 1, computing device 104 may classify the parasitic background 112 to the parasitic disease assessment 120 using the assessment classification machine-learning process 124 and assign the parasitic disease assessment 120 as a function of the classifying. For instance and without limitation, training data may include sets of parasitic biomarkers 108, as described above, for large cohorts of users, from a variety of locations. Assessment classification machine-learning process 124 may be trained with training data to determine algorithms for sorting parasitic background 112 as a function of trends in gene expression, SNPs, parasitic strains, user symptomology, nutritional deficiencies, current location(s), and the like. Such training data may originate from a variety of sources, for instance from user input via a health state questionnaire and a graphical user interface. Training data may originate from a biological extraction test result such as genetic sequencing from user stool samples, blood panel for metabolites, and the like Training data may originate from a user's medical history, a wearable device, a family history of disease, and the like. Training data may similarly originate from any source, as described above, for parasitic biomarker 108 and determining parasitic background 112.

Continuing in reference to FIG. 1, classification may include identifying which set of parasitic disease assessment 120 a parasitic background 112 observation, or set of observations, belongs. Classification may include clustering based on pattern recognition, wherein the presence of parasitic biomarkers 108 identified in parasitic background 112 relate to a particular parasitic disease assessment 120. Such classification methods may include binary classification, where the parasitic background 112 is simply matched to each existing parasitic disease assessment 120 and sorted into a category based on a "yes"/"no" match. Classification may include weighting, scoring, or otherwise assigning a numerical valuation to data elements in parasitic background 112 as it relates to each parasitic disease assessment 120. Such a score may represent a likelihood, probability, or other statistical identifier that relates to the classification into parasitic disease assessment 120, where the highest score may be selected depending on the definition of "highest". In this way, assessment classification machine-learning process 124 may be free to create new classification categories as a function of how well a user may be categorized to existing categories.

Continuing in reference to FIG. 1, computing device 104 is configured to determine a current position of the user. A "current position," as used in this disclosure, is a current physical location of a user. A current position 128 may include the current location of the user, with varying levels of granularity, such as a home or building address, a city, territory, country, and the like Computing device 104 may determine a current position 128 of a user by using a mapping algorithm, application, web-based mapping tool, or the like, for instance and without limitation, GOOGLE MAPS and a web browser, communicating with GPS via the Internet and Wi-Fi connectivity on a user device, and the like Determining a current position 128 may include receive input via computing device 104, such as entering a datum of text, issuing a command, or specifying a 2D position, for instance on a map. User may input such data via a graphical user interface and user device. Determining a current position 128 may include retrieving location data of the user throughout the day, week, month, and the like, to determine where the current position 128 of the user had been. Such data may be stored and/or retrieved from a database.

Continuing in reference to FIG. 1, computing device 104 is configured to identify, using the current position 128 and the parasitic disease assessment 120, a parasitic infection intervention. A "parasitic infection intervention," as used in this disclosure, is at least a nutrition element intended to be consumed by the user to address a parasitic infection. A "nutrient element," as used herein, is an item that contains at least a nutrient amount. A "nutrient amount," as used in this disclosure, is a numerical value(s) relating to the amount of a nutrient. A "nutrient," as used in this disclosure, is any biologically active compound whose consumption is intended to have an effect on the user. An intended effect may include reducing the population of a microorganism which may include slowing the growth rate, undoing colonization, depleting the population, suppressing growth by improving immunological function, clearance of parasite eggs, larvae, altering neutrophil activity, altering macrophage activity, improving Th2 response, and the like. Parasitic infection intervention 132 may "address parasitic infection" by treating a current infection, for instance by indicating to user a particular nutrition element for assisting in treating a symptom or reverse an infection. Parasitic infection intervention 132 may address parasitic infection by proving nutrition elements intended to prevent infection.

Continuing in reference to FIG. 1, identifying a parasitic infection intervention 132 includes calculating a first parasitic infection rate as a function of the current position 128. A "parasitic infection rate," as used in this disclosure, is a determination about the incidence of parasitic infection as a function of a location. For instance, a first parasitic infection rate 136 may include a current position 128. A first parasitic infection rate 136 may include a numerical value, such as a score describing the incidence and/or risk of a particular parasitic infection and/or a particular region. A first parasitic infection rate 136 may include a function describing the risk as a function of time for a region, for instance, describing patterns and trends in the incidence rate of malaria infection in a sub-tropical region, over the course of the year.

Continuing in reference to FIG. 1, calculating the first parasitic infection rate 136 may include training an infection rate model using an intervention machine-learning process and training data, wherein training data includes a plurality of data entries of parasitic disease assessments correlated to a plurality of locations. Infection rate model 140 may include any machine-learning algorithm and/or model described herein. Infection rate model 140 may be generated by intervention machine-learning process which may include any machine-learning process, algorithm, and/or method performed by machine-learning module as described in further detail below. Training data for infection rate model 140 may include a plurality of data entries which include parasitic disease assessments, such as parasitic categories, parasite biomarker levels among users, and the like, correlated to a plurality of locations. Plurality of locations may refer to continental regions such as "Africa", "Asia", "Europe", and the like Plurality of locations may include individual countries, territories, regions such as "Tropical", "Sub-tropical", "Tundra", "Freshwater region", and the like Such training data may originate from municipal health departments, Centers for Disease Control (CDC), World Health Organization (WHO), peer-reviewed research databases, physicians, hospitals, and the like. Training data may originate from a plurality of parasitic disease assessments from a plurality of users, wherein with each parasitic disease assessment from increased participation in system 100, computing device 104 may generate a more accurate infection rate model 140.

Continuing in reference to FIG. 1, calculating the first parasitic infection rate 136 may include calculating the first parasitic infection rate 136 as a function of the current position 128 and the infection rate model 140. Computing device 104 may accept an input of the current position 128 and generate an output that is the first parasitic infection rate 136 as a function of the infection rate model 140. First infection rate 136 may be compared to a threshold value, for instance and without limitation, below which there is 'no imminent risk of parasitic infection'. Such a threshold value may be used to directly compare between a plurality of current positions 128 between users. Calculating may include mathematical operations, such as subtraction, wherein computing device 104 may compare infection rate model 140 parasitic infection rates to a threshold value to determine if a current position 128 represents a "higher than average risk", "below average risk", and the like Calculating may include using infection rate model 140 to derive an algorithm, equation, and/or function that describes, for any current position 128 and parasitic disease assessment 120, the infection rate as it relates to a per-user basis. Each user may not experience congruent parasitic infection rate despite sharing the same current position 128. For instance, users may differ in immunocompromised state, current parasitic infection, symptoms, nutrition deficiency, and the like, which may alter risk.

Continuing in reference to FIG. 1, identifying parasitic infection intervention 132 includes determining at least a first nutrient amount as a function of the first parasitic infection rate 136 and the parasitic disease assessment 120. A "first nutrient amount," as used in this disclosure, is a quantity of a nutrient amount that is intended to address the first parasitic infection rate 136 as a function of a parasitic disease assessment 120. First nutrient amount 144 may include a mass amounts of a vitamin, mineral, macronutrient (carbohydrate, protein, fat), micronutrient. First nutrient amount 144 may include a numerical value for describing a value of calories. First nutrient amount 144 may include numerical values described mass amounts of phytonutrients, antioxidants, bioactive ingredients, nutraceuticals, and the like. First nutrient amount 144 may include activity, or active, amounts such as "units" of digestive enzymes (IU).

Continuing in reference to FIG. 1, determining the at least a first nutrient amount 144 may include training a parasitic infection intervention model using an infection machine-learning process and training data, wherein training data includes a plurality of data entries of nutrition amounts correlated to addressing parasitic infection. Parasitic infection model 148 may include any machine-learning algorithm and/or model described herein. Parasitic infection model 148 may be generated by infection machine-learning process which may include any machine-learning process, algorithm, and/or method performed by machine-learning module as described in further detail below. Training data for parasitic infection model 148 may include a plurality of data entries which include nutrient amounts, such as mg/kg nutraceuticals, correlated to effects of addressing parasitic infections. For instance and without limitation, training data may include a variety of nutrient amounts of phytonutrients, antioxidants, nutraceuticals, and/or bioactive ingredients from garlic, such as diallyl thiosulfate (allicin), diallyl sulfide (DAS), diallyl disulfide (DADS), diallyl trisulfide (DATS), E/Z-ajoene, S-allyl-cysteine (SAC), and S-allyl-cysteine sulfoxide (alliin), from ginger such as 6-gingerol, 8-gingerol, 10-gingerol, 6-shogaol, 6-paradol, polyphenols, among other aromatic constituents including zingiberene, bisabolene, and the like, wherein the nutrient amounts are correlated to in vivo and in vitro activity against parasites. Such training data may also include the relative amounts of such nutrients found in nutrition elements, as well as the amounts, post-consumption, found in the blood, bile, GI tract, and the like, where a parasite infection may be in the user. In this case, parasitic infection intervention model 148 may include being trained with training data that includes pharmacokinetics and pharmacognosy data relating to medicinal compounds and/or bioactive ingredients from plants such as consumable vegetables, fruits, seeds, and the like, which informs, post-consumption nutrient amounts in the user. Such training data may originate from any source described herein, such as from peer-reviewed research, a database, via a web browser and the Internet by a guided query, provided by a dietician, wearable device, and the like.

Continuing in reference to FIG. 1, determining the at least a first nutrient amount 144 may include determining the at least a first nutrient amount 144 as a function of at least the parasitic disease assessment 120 and the parasitic infection intervention model 148. Computing device 104 may accept an input of the parasitic disease assessment 120 and generate an output of the at least a first nutrient amount as a function of the parasitic infection intervention model 148. Alternatively or additionally, computing device 104 may accept an input of the parasitic disease assessment 120 and first parasitic infection rate 136 and generate an output of the at least a first nutrient amount 144 as a function of the parasitic infection intervention model 148. In such a case, nutrient amounts may then change as a function of current position 128 according to parasitic infection rates at current position 128.

Continuing in reference to FIG. 1, identifying a parasitic infection intervention 132 includes identifying at least a first nutrition element that includes the at least a first nutrient amount 144. A "first nutrition element," as used in this disclosure, is a nutrition element that includes the at least a first nutrient amount 144. For instance and without limitation, first nutrition element 152 may include, for instance as described above, garlic, ginger, or any number of plant-based nutrition elements that nutrient amounts may be identified for.

Continuing in reference to FIG. 1, identifying the at least a first nutrition element 152 may include training a nutrition model using a nutrition machine-learning process and training data, wherein training data includes a plurality of data entries of nutrition amounts correlated to nutrition elements. Nutrition model 156 may include any machine-learning algorithm and/or model described herein. Nutrition model 156 may be generated by nutrition machine-learning process which may include any machine-learning process, algorithm, and/or method performed by machine-learning module as described in further detail below. Training data for nutrition model 156 may include a plurality of data entries which include nutrient amounts correlated to nutrition elements. For instance and without limitation, training data may include a plurality of meals, menu items, food groups such as 'dairy, 'animal-products, 'vegetables', and the like, correlated to nutrient amounts. Training data may include nutrient amounts such as macronutrients and micronutrients from nutrition facts. Training data may include nutrient amounts that are not traditionally reported in nutrition facts, that a typical consumer may not be aware, such as polyphenols, antioxidants, bicarbonate, and the like. Such training data may originate from any source described herein, such as from peer-reviewed research, a database, via a web browser and the Internet by a guided query, provided by a dietician, wearable device, and the like.

Continuing in reference to FIG. 1, identifying the at least a first nutrition element may include identifying the at least a first nutrition element 152 as a function of the at least a first nutrient amount 144 and the nutrition model 156. Computing device 104 may accept an input of the at least a first nutrient amount 144 and generate an output of the at least a first nutrition element 152 as a function of the nutrition model 156.

Continuing in reference to FIG. 1, computing device 104 is configured to receive a geophysical indicator relating to the user. A "geophysical indicator," as used in this disclosure, is an indication about a user concerning a change in location. Geophysical indicator 160 may include current position 128, for instance and without limitation, as a future designated time, updated from when the current position 128 was originally indication, and/or altered by a weighting factor controlling for updated parasitic infection data. Geophysical indicator 160 may include a location a user is planning to travel to in the future for vacation, work, and the like Geophysical indicator 160 may include GPS coordinates, latitude and/or longitude coordinates, addresses, cities, countries, and the like. Geophysical indicator 160 may originate from the user, for instance as user input with computing device 104 via a user interface. Geophysical indicator 160 may include data from a third-party source such as synched from a calendar application on a user device, retrieved from a database that collects positional data relating to user, and the like. Determining a current location 128, as described above, may be performed with geophysical indicator 160.

Continuing in reference to FIG. 1, computing device 104 is configured to identify, using the geophysical indicator 160, a parasitic prevention strategy, wherein determining the parasitic prevention strategy includes calculating a second parasitic infection rate as a function of the geophysical indicator 160. A "parasitic prevention strategy," as used in this disclosure, is at least a nutrition element intended to be taken by the user to prevent parasitic infection. Parasitic prevention strategy may include nutrition elements that contain nutrient amounts intended to prevent parasitic infection in the user as a prophylaxis. Parasitic prevention strategy 164 may be generated as a function of a first parasitic infection rate 136 from current position 128 and a second parasitic infection rate which also corresponds to current position 128. A second parasitic infection rate 168 may include a numerical value, such as a score describing the incidence and/or risk or a particular parasitic infection and/or a particular region. A second parasitic infection rate 168 may include a function describing the risk as a function of time for a region, for instance, describing patterns and trends in the incidence rate of parasitic infection in a region. Calculating second parasitic infection rate 168 may include any method and/or process for calculating first parasitic infection rate 136, as described above.

Continuing in reference to FIG. 1, identifying the parasitic prevention strategy includes comparing the first parasitic infection rate 136 of the current position 128 and the second parasitic infection rate 168 of the geophysical indicator 160. Comparing may be performed using a mathematical operation, such as subtraction, wherein the parasitic infection rates may include numerical values that are subtracted from one another to determine if travel from current location 128 to geophysical indicator 160 presents increased parasitic infection rate and/or for which category of parasitic infection. Comparison may include any pairwise comparison method, including for instance and without limitation, probability models and forecasts, which make determinations about the geographical indicator 160 as a "future current location." The "future current location" may include current position 128. In such an instance, parasitic prevention strategy 168 may include a second parasitic infection rate 168 that is updated, weighted, or otherwise calculated from a first parasitic infection rate 136 as an input. Infection rate model 140 used to determine first parasitic infection rate 136 may generate second parasitic infection rate 168 using current position 128 for each.

Continuing in reference to FIG. 1, comparing the first parasitic infection rate 136 and the second parasitic infection rate 168 may include calculating a difference in parasitic infection rate as a function of difference in location between the current position 128 and the geophysical indicator 160. In non-limiting illustrative embodiments, computing device 104 may store and/or retrieve parasitic infection rates classified by location, such as region, country, state, and the like, and iteratively compare current location 128 and geophysical indicator 160, as a function of sampling all parasitic infection rates that exist for all regions. For instance and without limitation, computing device may calculate a difference in parasitic infection rate as a function of difference in location by retrieving a "seed location," for instance a first location nearby geophysical location 160 and using regression analysis with a cluster of nearby locations, derive a more specific and accurate difference in parasitic infection rate between current position 128 and regions nearby geophysical indicator 160 to approximate. In this way, computing device 104 may generate a forecast of parasitic infection rates and incidence, for a plurality of locations, throughout the year. With greater data sets, computing device 104 may use machine-learning, such as multiple linear regression models, with training data including a plurality of data entries correlating parasitic incidence to locations and map analyses to predict infection rates worldwide. In this way, computing device 104 may retrieve such analyses from a database and calculate a difference between any two or more locations. Such training data may originate from any source described herein, such as municipal health officials, Center for Disease Control (CDC), World Health Organization (WHO), peer-reviewed research, and the like.

Continuing in reference to FIG. 1, identifying the parasitic prevention strategy 164 includes determining at least a second nutrient amount as a function of the comparison. A "second nutrient amount," as used in this disclosure, is a quantity of a nutrient that is intended to prevent parasitic infection according to comparison in parasitic infection rate between locations. Second nutrient amount 172 may be determined, identified, or otherwise calculated as first nutrient amount 144 is calculated, as described herein. Second nutrient amount 172 may include any nutrient amount that may represent a first nutrient amount 144.

Continuing in reference to FIG. 1, determining the at least a second nutrient amount 172 may include training a parasitic prevention model using a prevention machine-learning process and training data, wherein training data includes a plurality of data entries of regional nutrition elements correlated to rates of parasitic infection. Parasitic prevention model 176 may include any machine-learning algorithm and/or model described herein. Parasitic prevention model 176 may be generated by prevention machine-learning process which may include any machine-learning process, algorithm, and/or method performed by machine-learning module as described in further detail below. Training data for parasitic prevention model 176 may include a plurality of data entries which include regional nutrition elements correlated to preventing parasitic infection. For instance and without limitation, training data may include a plurality of regional goods, meals, menu items, food groups such as 'dairy, 'animal-products, 'vegetables', 'water sources', and the like, correlated to varying effects on parasitic infection, including parasitic infection likelihood, rate, and/or preventing parasitic infection. "Regional nutrition elements," as used in this disclosure, is a nutrition element that is related by proximity to a location for which an infection rate is associated. Regional nutrition elements may include unique elements of cuisine found around a geophysical indicator 160. Training data may include nutrient amounts such as macronutrients and micronutrients from nutrition facts, from ingredients lists of local dishes, snacks, and the like. Training data may include nutrient amounts that are not traditionally reported in nutrition facts, that a typical consumer may not be aware, such as polyphenols, antioxidants, and the like, as described above. Such training data may originate from any source described herein, such as from peer-reviewed research, a database, via a web browser and the Internet by a guided query, provided by a dietician, wearable device, and the like. Parasitic prevention model 176 may derive relationships regarding prevention of parasitic infection from use of local plants, animal products, and the like. Correspondingly, parasitic prevention model 176 may identify water sources, nutrition elements, and the like, which contribute to parasitic infection at a geophysical indicator 160.

Continuing in reference to FIG. 1, determining the at least a second nutrient amount 172 may include determining the at least a second nutrient amount 172 amount as a function of at least the geophysical indicator 160 and the parasitic prevention model 176. Computing device 104 may accept an input of geophysical indicator 160 and generate an output of the at least a second nutrient amount 172 as a function of the parasitic prevention model 176.

Continuing in reference to FIG. 1, identifying a parasitic prevention strategy 164 may include identifying at least a second nutrition element that includes the at least a second nutrient amount 172. A "second nutrition element," as used in this disclosure, is a nutrition element that includes the at least a second nutrient amount 172. For instance and without limitation, second nutrition element 180 may include, for instance as vitamin A, zinc, and/or any number of nutrition elements that nutrient amounts may be identified for.

Continuing in reference to FIG. 1, identifying the at least a second nutrition element 180 may include any process and/or method described herein for identifying the at least a first nutrition element 152, for instance the nutrition model 156 generating by nutrition machine-learning process and training data, wherein training data includes a plurality of data entries of nutrition amounts correlated to nutrition elements. Nutrition model 156 may identify nutrition elements as a function of the relationships observed between nutrition elements and nutrient amounts. Computing device 104 may accept an input of the at least a second nutrient amount 172 and generate an output of the at least a second nutrition element 180 as a function of the nutrition model 156. Alternatively or additionally, computing device 104 may query for the at least a second nutrition element 180, for instance using a web browser and the Internet, using an input of the at least a second nutrient amount 172. Computing device 104 may store and/or retrieve the at least a second nutrition element 180 from a database as a function of the at least a second nutrient amount 172 as an input.

Continuing in reference to FIG. 1, computing device 104 is configured to generate a parasitic infection nutrition program, using the parasitic infection intervention 132 and the parasitic prevention strategy 164. A "parasitic infection nutrition program," as used in this disclosure, is a plurality of nutrition elements as dietary recommendations according to the parasitic infection intervention 132 and the parasitic prevention strategy 164. Parasitic infection nutrition program 184 may include a "frequency," which as used in this disclosure, is a timing associated with at least a nutrition element. Parasitic infection nutrition program 184 includes a "magnitude," which as used in this disclosure, is an amount of nutrient amount. A frequency may include daily scheduled meals, beverages, health shakes, and the like. A magnitude may include serving sizes, mass amounts of vitamins and minerals, and the like. Parasitic infection nutrition program 184 may include a frequency and timing associated with the at least a first nutrition element 152 and the at least a first nutrition element 180.

Continuing in reference to FIG. 1, generating the parasitic infection nutrition program 184 may include generating an objective function with the parasitic infection intervention 132, the parasitic prevention strategy 164, wherein the objection function outputs at least an ordering of a nutrition elements according to constraints of the current position 128 and the geophysical indicator 160. An "objective function,"

as used in this disclosure, is a mathematical function that may be used by computing device 104 to score each possible combination of nutrition elements, wherein the objective function may refer to any mathematical optimization (mathematical programming) to select the 'best' element from a set of available alternatives. Selecting the 'best' element from a set of available alternatives may include a combination of nutrition elements which achieves the nutrient amounts in addressing parasitic infection intervention 132, parasitic prevention strategy 164, and/or parasitic background 112 in a user.

Continuing in reference to FIG. 1, in non-limiting illustrative examples, an objective function may include performing a greedy algorithm process. A "greedy algorithm" is defined as an algorithm that selects locally optimal choices, which may or may not generate a globally optimal solution. For instance, computing device 104 may select combinations of nutrition elements so that values associated therewith are the best value for each category. For instance, in non-limiting illustrative example, optimization may determine the combination of the most efficacious 'serving size', 'timing of consumption', 'phytonutrient', among other categories, to provide a combination that may include several locally optimal solutions but, together, may or may not be globally optimal in combination.

Still referring to FIG. 1, in further non-limiting illustrative examples, objective function may be formulated as a linear objective function, which computing device 104 may solve using a linear program, such as without limitation, a mixed-integer program. A "linear program," as used in this disclosure, is a program that optimizes a linear objective function, given at least a constraint; a linear program may be referred to without limitation as a "linear optimization" process and/or algorithm. For instance, in non-limiting illustrative examples, a given constraint might be a metabolic disorder of a user such as lactose intolerance, poor nutrient absorption, food allergy, and the like, and a linear program may use a linear objective function to calculate ingredient combinations, considering how these limitations effect combinations. In various embodiments, system 100 may determine a set of instructions towards building parasitic infection nutrition program 184 that maximizes a total infection prevention subject to a constraint that there are other competing objectives, wherein "maximizing" the score may be performed according to the numerical scale, and what criteria is used for "high" and "low" scores. For instance, if achieving one nutrient amount and a second nutrient amount may result in needing to select a first nutrition element and a second nutrition element, wherein each may compete in preventing parasitic infection (e.g. adopting two or more diet types simultaneously may not be feasible, addressing infection of one parasite supports growth of a potential second parasitic organism, and the like). A mathematical solver may be implemented to solve for the set of instructions that maximizes scores; mathematical solver may be implemented on computing device 104 and/or another device in system 100, and/or may be implemented on third-party solver.

With continued reference to FIG. 1, in further non-limiting illustrative examples, objective function may include minimizing a loss function, where a "loss function" is an expression of an output which a process minimizes to generate an optimal result. For instance, achieving a first nutrient amount 144 and a second nutrient amount 172 may be set to a nominal value, such as '100', wherein the objective function selects elements in combination that reduce the value to '0', wherein the nutrient amounts are '100% achieved'. In such an example, 'maximizing' would be selecting the combination of nutrition elements that results in achieving nutrient amounts by minimizing the difference, where suboptimal pairing results in score increases. As a non-limiting example, computing device 104 may assign variables relating to a set of parameters, which may correspond to parasitic infection nutrition program 184 components, calculate an output from a mathematical expression using the variables, and select an objective that produces an output having the lowest size, according to a given definition of "size." Selection of different loss functions may result in identification of different potential combinations as generating minimal outputs, and thus 'maximizing' efficacy of the combination.

Figure 2:
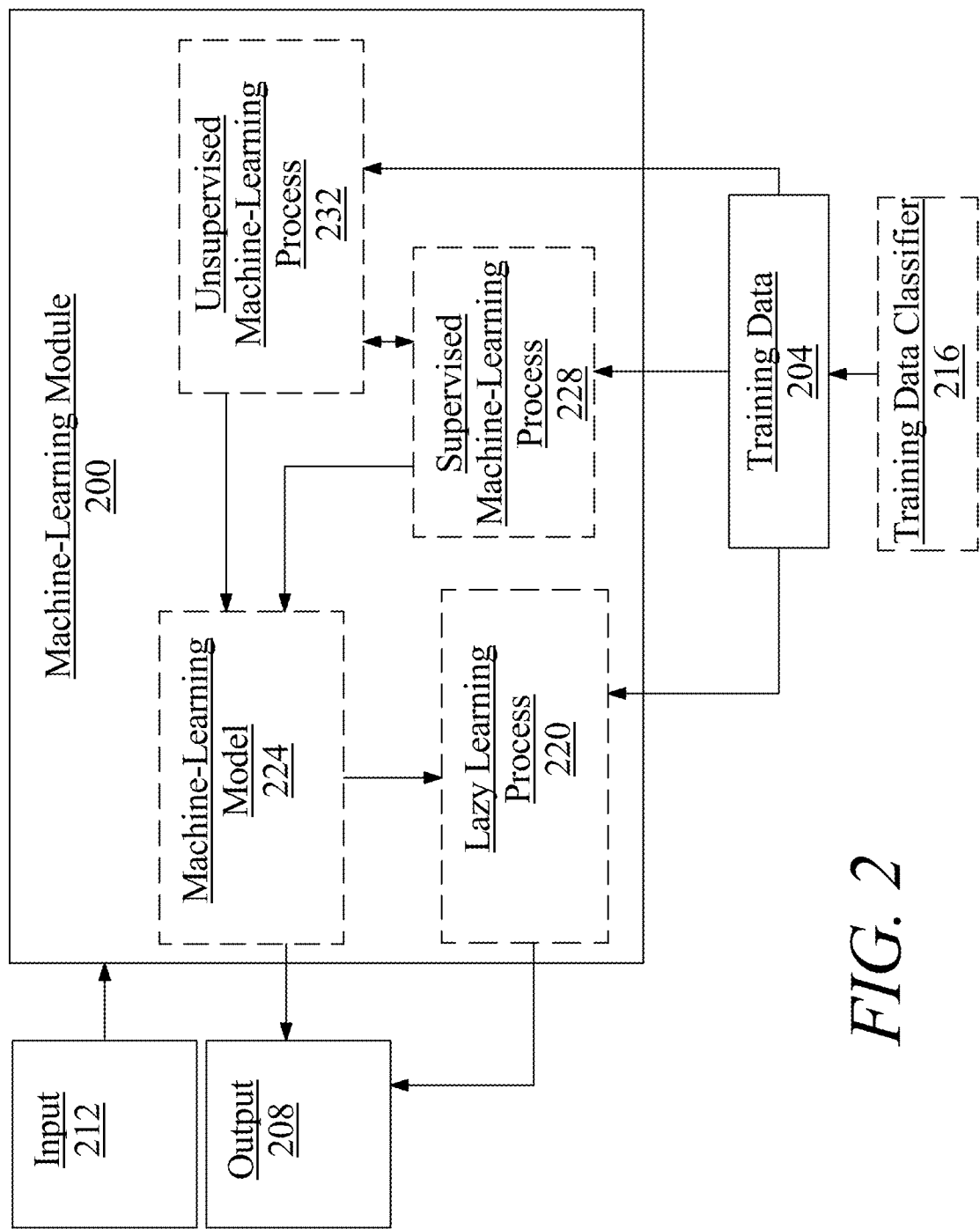
FIG. 2 is a block diagram illustrating a machine-learning module.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device/module to produce outputs 208 given data provided as inputs 212; this is in contrast to a non-machine learning software program where the commands to be executed are determined in advance by a subject and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail herein. Training data 204 used by machine-learning module 200 may correlate any input data as described in this disclosure to any output data as described in this disclosure.

Further referring to FIG. 2, training data may be filtered, sorted, and/or selected using one or more supervised and/or unsupervised machine-learning processes and/or models as described in further detail herein; such models may include without limitation a training data classifier 216. Training data classifier 216 may include a "classifier," which as used in this disclosure is a machine-learning model as defined herein, such as a mathematical model, neural net, or program generated by a machine learning algorithm known as a "classification algorithm," as described in further detail herein, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a process whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to elements that characterizes a sub-population, such as a subset of parasitic biomarkers 108 such as patterns in cytokine levels, gene expression, and the like, as it relates to parasitic background 112, parasitic disease assessment 120, and/or other analyzed items and/or phenomena for which a subset of training data may be selected.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of predictions may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements, such as classifying parasitic biomarker 108 elements to parasitic background 112 elements and assigning a value as a function of some ranking association between elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail herein.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. A machine-learning model may be used to derive numerical scales for providing numerical values to parasitic background 112, parasitic infection rates, and the like, as described herein, to "learn" the upper and lower limits to the numerical scale, the increments to providing scoring, and the criteria for increasing and decreasing elements encompassed in the parasitic background 112, first parasitic infection rate 136, second parasitic infection rate 168, and the like A machine-learning model may be used to "learn" which elements of parasitic biomarkers 108 have what effect on parasitic background 112, and which elements of parasitic background 112 are affected by particular nutrition elements and the magnitude of effect, and the like The magnitude of the effect may be enumerated and provided as part of system 100, where nutrition elements are communicated to user for their parasitic infection properties.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a parasitic background 112 (potentially classified into parasitic disease assessment 120), as described above as inputs, nutrient amount outputs, and a ranking function representing a desired form of relationship to be detected between inputs and outputs; ranking function may, for instance, seek to maximize the probability that a given input and/or combinations of inputs is associated with a given output to minimize the probability that a given input is not associated with a given output, for instance finding the most suitable times to consume meals, and what the meals should be, and the like Ranking function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning process 232. An unsupervised machine-learning process 232, as used herein, is a process that derives inferences in datasets without regard to labels; as a result, an unsupervised machine-learning process 232 may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 204.

Figure 3:
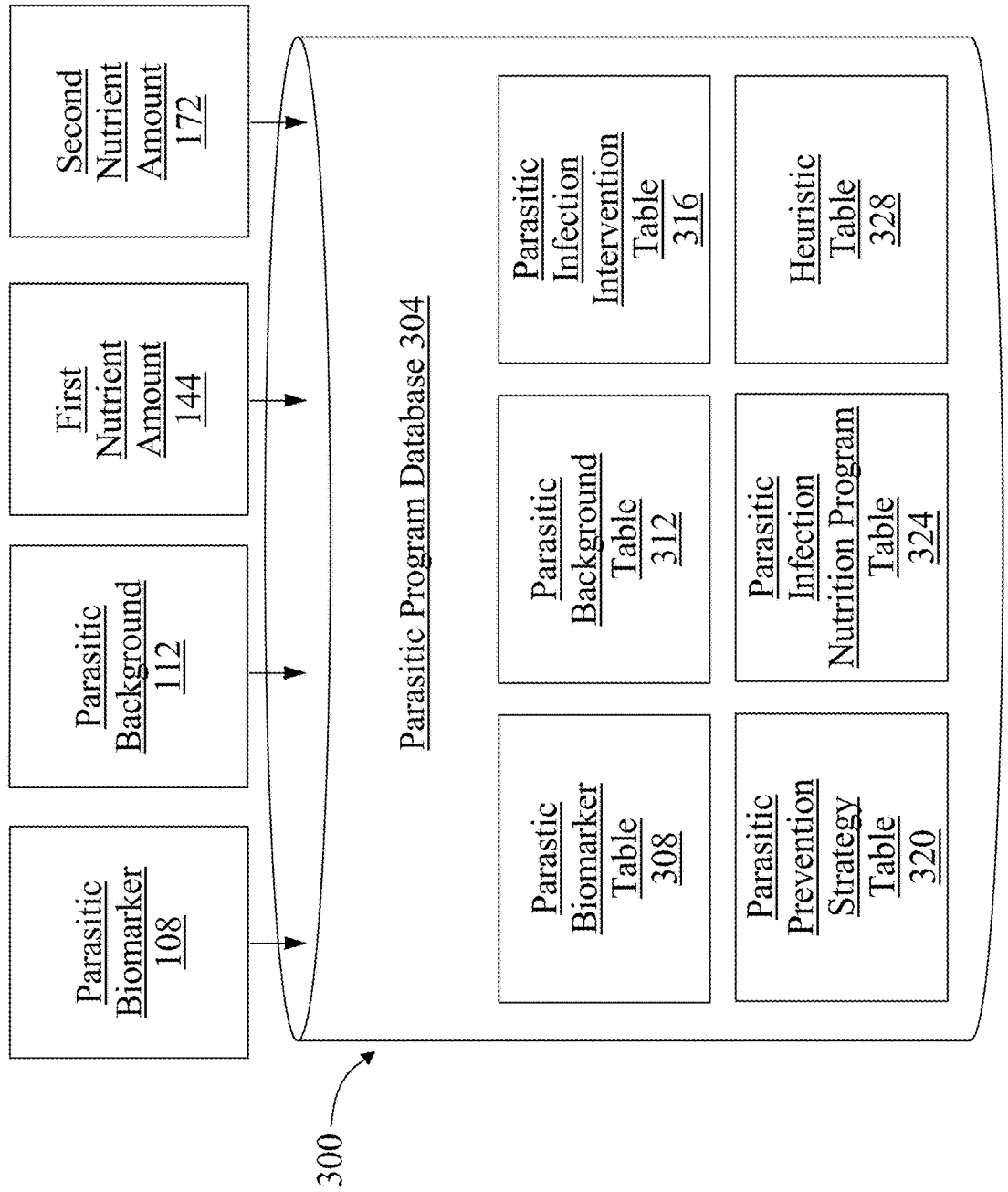
FIG. 3 is a block diagram of a parasitic program database.

Referring now to FIG. 3, a non-limiting exemplary embodiment 300 of a parasitic program database 304 is illustrated. Parasitic biomarker 108 for a plurality of subjects, for instance for generating a training data classifier 216, may be stored and/or retrieved in parasitic program database 304. Parasitic biomarker 108 data from a plurality of subjects for generating training data 204 may also be stored and/or retrieved from parasitic program database 304. Computing device 104 may receive, store, and/or retrieve training data 204, wearable device data, physiological sensor data, biological extraction data, and the like, from parasitic program database 304. Computing device 104 may store and/or retrieve machine-learning models, classifiers, among other determinations, I/O data, heuristics, algorithms, and the like, from parasitic program database 304.

Continuing in reference to FIG. 3, parasitic program database 304 may be implemented, without limitation, as a relational database, a key-value retrieval database such as a NOSQL database, or any other format or structure for use as a database that a person skilled in the art would recognize as suitable upon review of the entirety of this disclosure. Parasitic program database 304 may alternatively or additionally be implemented using a distributed data storage protocol and/or data structure, such as a distributed hash table and the like. Parasitic program database 304 may include a plurality of data entries and/or records, as described above. Data entries in parasitic program database 304 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistent with this disclosure.

Further referring to FIG. 3, parasitic program database 304 may include, without limitation, parasitic biomarker table 308, parasitic background table 312, parasitic infection intervention table 316, parasitic prevention strategy table 320, parasitic infection nutrition program table 324, and/or heuristic table 328. Determinations by a machine-learning process, machine-learning model, ranking function, and/or classifier, may also be stored and/or retrieved from the parasitic program database 304. As a non-limiting example, parasitic program database 304 may organize data according to one or more instruction tables. One or more parasitic program database 304 tables may be linked to one another by, for instance in a non-limiting example, common column values. For instance, a common column between two tables of parasitic program database 304 may include an identifier of a submission, such as a form entry, textual submission, accessory device tokens, local access addresses, metrics, and the like, for instance as defined herein; as a result, a search by a computing device 104 may be able to retrieve all rows from any table pertaining to a given submission or set thereof. Other columns may include any other category usable for organization or subdivision of data, including types of data, names and/or identifiers of individuals submitting the data, times of submission, and the like; persons skilled in the art, upon reviewing the entirety of this disclosure, will be aware of various ways in which data from one or more tables may be linked and/or related to data in one or more other tables.

Continuing in reference to FIG. 3, in a non-limiting embodiment, one or more tables of parasitic program database 304 may include, as a non-limiting example, parasitic biomarker table 308, which may include categorized identifying data, as described above, including genetic data, epigenetic data, parasitic infection data, physiological data, biological extraction data, and the like. Parasitic biomarker table 308 may include parasitic biomarker 108 categories according to gene expression patterns, SNPs, mutations, cytokine concentration, travel data, data concerning metabolism of nutrition elements, pharmacokinetics, nutrient absorption, and the like, categories, and may include linked tables to mathematical expressions that describe the impact of each parasitic biomarker 108 datum on parasitic background 112, for instance threshold values for gene expression, and the like, as it relates to parasitic disease assessment 120, and the like Parasitic biomarker table 308 may include genus, species, serotype, and the like, listing of parasitic microorganisms. One or more tables may include parasitic background table 312, which may include data regarding parasitic biomarker 108, thresholds, scores, metrics, values, categorizations, and the like, that system 100 may use to calculate, derive, filter, retrieve and/or store parasitic disease assessments 120, identifiers related with cohorts of users, and the like. One or more tables may include parasitic infection intervention table 316, which may include data on nutrient amounts, nutrient amount effects on parasitic infection, and nutrient elements for addressing parasitic infection, for instance classified as a function of parasitic disease assessment 120, classified to data from alike users with similar parasitic biomarker(s) 104 and/or parasitic background 112, and the like, that system 100 may use to calculate, derive, filter, retrieve and/or store. One or more tables may include parasitic prevention strategy table 320, which may nutrient amounts, nutrient amount effects on preventing parasitic infection, and nutrient elements for preventing parasitic infection, for instance classified as a function of parasitic disease assessment 120, classified to data from alike users with similar parasitic biomarker(s) 104 and/or parasitic background 112, and the like, that system 100 may use to calculate, derive, filter, retrieve and/or store. One of more tables may include parasitic infection nutrition program table 324, which may include nutrition element identifiers, parasitic infection nutrition program 184, parasitic infection intervention 132, parasitic prevention strategy 164, associated nutrient amounts and/or nutrition elements for address and/or prevent parasitic infection, frequency and magnitudes associated with nutrition elements, regarding times to eat, identifiers of meals, recipes, ingredients, diet types, and the like. One or more tables may include, without limitation, a heuristic table 328, which may organize rankings, scores, models, outcomes, functions, numerical values, scales, arrays, matrices, and the like, that represent determinations, probabilities, metrics, parameters, values, standards, indexes, and the like, include one or more inputs describing potential mathematical relationships, as described herein.

Figure 4A:
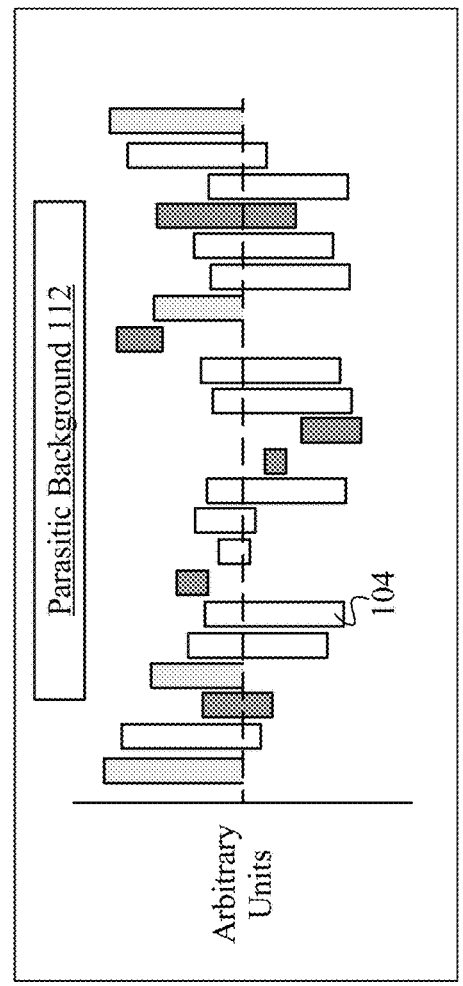
FIGS. 4A and 4B are a diagrammatic representation of a parasitic background.
Figure 4B:
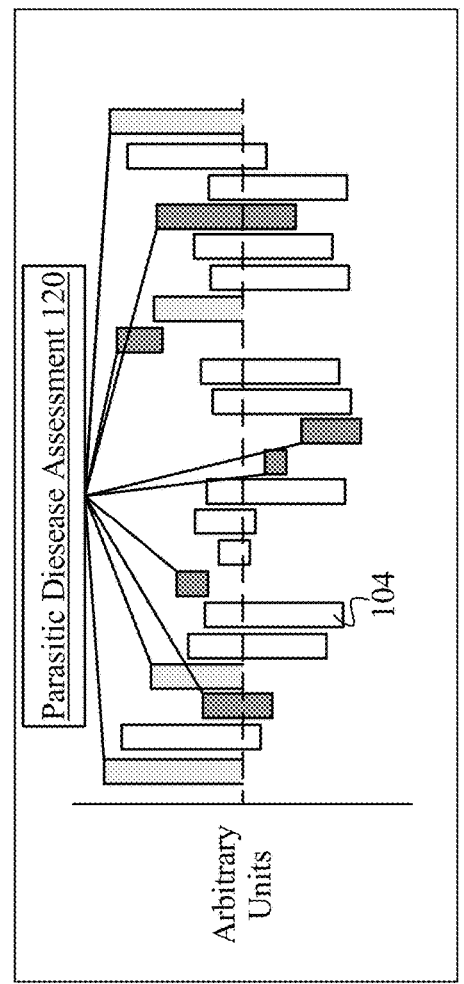

Referring now to FIGS. 4A and 4B, a non-limiting exemplary embodiment 400 of a parasitic background 112 is illustrated. Parasitic background 112 may include a variety of parasitic biomarker 108 categories, for instance 22 distinct categories, as shown in FIGS. 4A and 4B. each parasitic biomarker 108 may be assigned a parameter and/or value, such as an arbitrary value, where some parasitic biomarkers 108, such as those shaded in light grey, may relate to absolute scales from [0, x], where x is a maximal value and the range of values for the parasitic biomarker 108 cannot be below a 'zero amount'. Some parasitic biomarkers 108, such as those shaded in dark grey, may relate to gene expression levels, wherein, the parasitic biomarker 108 is enumerated as a 'box plot' that illustrates the range of expression in a population of users organized according to, for instance parasitic disease assessment 120. In such an example, the dashed line may relate to a 'normal threshold' above which is elevated gene expression of the user, below which is decreased expression level. Each parasitic biomarker 108 may have associated with it a numerical score, or some other identifying mathematical value, variable, and/or expression that computing device 104 may assign. Persons skilled in the art, upon benefit of this disclosure in full, may appreciate that for each user, any number of parasitic biomarkers 108 may be enumerated and assigned a value according to parasitic background machine-learning model 116. Parasitic background 112 may be graphed, or otherwise displayed, according to the enumeration by parasitic background machine-learning model 116. For instance, each bar of the bar graph, or combinations of bar graph categories, may instruct a classification of a user's parasitic background 112 to parasitic disease assessment 120.

Still referring now to FIGS. 4A and 4B, in non-limiting exemplary illustrations, parasitic background 112 may be classified to parasitic disease assessment 120. Some and/or all of the parasitic biomarkers 108 summarized in parasitic background 112 may be used to classify an individual to a particular parasitic disease assessment 120. For instance, as shown in FIG. 4B, ten of the 22 parasitic biomarker 108 categories may be used to classify parasitic background 112 to one or more subsets of parasitic infection type, for instance, categorization based on parasitic infection prevalence based on current location 128, or geophysical indicator 160, such as hookworm, malaria, Chagas Disease, among many other classifications. Alternatively or additionally, parasitic background machine-learning model 116 may be trained to assign parasitic biomarker 108 to parasitic disease assessment 120, wherein computing device 104 may know the identity of parasitic disease assessment 120 according to which parasitic disease assessment 120 has the most identifying data points.

Figure 5:
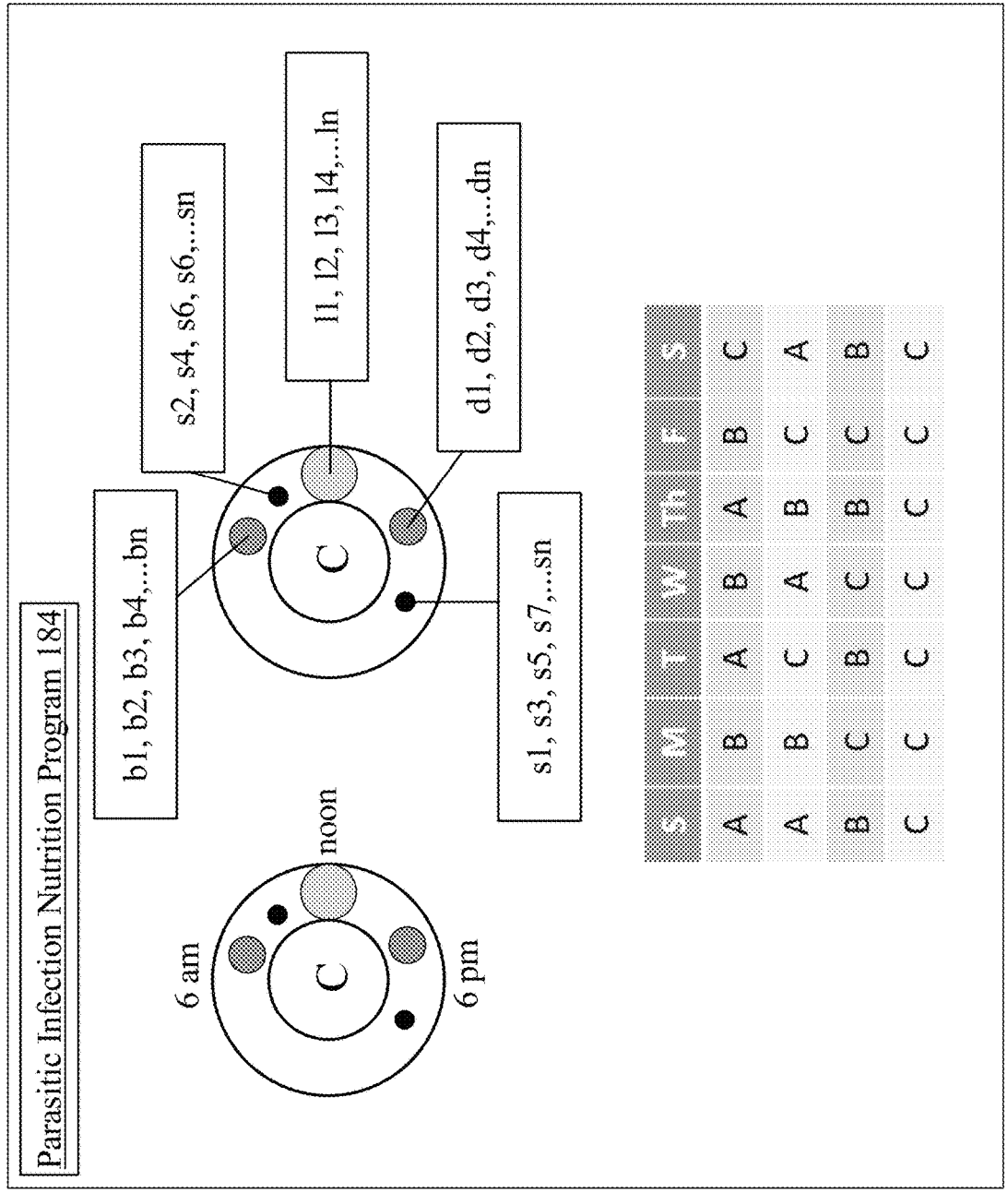
FIG. 5 is a diagrammatic representation of a parasitic infection nutrition program.

Referring now to FIG. 5, a non-limiting exemplary embodiment 500 of parasitic infection nutrition program 184 is illustrated. Parasitic infection nutrition program 184 may include a schedule for arranging nutrition elements, according to for instance a 24-hour timetable, as designated on the left, where consumption is planned along a user's typical day-night cycle, beginning at ~6 am until just after 6 pm. Nutrition element may include breakfast (denoted as mid-sized dark grey circle), which may correspond to a file of a plurality of breakfast-related first nutrition elements 152 and/or second nutrition elements 180 (denoted b1, b2, b3, b4 . . . bn, to the nth breakfast item). Nutrition element may include a first subset of snacks eaten throughout the day to, for instance supplementing nutrient amounts, such as phytonutrients, antioxidants, polyphenols, probiotics, and the like, (denoted as small black circles), which may correspond to a file of snacking-related nutrition elements for addressing a current parasitic infection and preventing parasitic infection as a function of geophysical indicator 160 (denoted s1, s2, s3, s4, s5, s6, s7, s8 . . . sn, to the nth snacking item). Nutrition element may include dinner (denoted as large-sized light grey circle), which may correspond to a file of dinner-related nutrition elements (denoted d1, d2, d3, d4 . . . dn, to the nth dinner item). Parasitic infection nutrition program 184 may include a variety of diets, as denoted in the monthly schedule at the bottom, Sunday through Saturday. Parasitic infection nutrition program 184 'C.' is shown, which may be an idealistic goal for user to achieve by the end of the month, where elimination-based plans 'A' and supplementation-based plans 'B' are intermediate plans optimized for addressing parasitic disease state, symptomology, and/or current position 128 parasitic infection rates. Nutrition elements classified by 'meal type' may be further modified by 'A' and 'B' according to user preferences collected by computing device 104 throughout the process. Circle sizes, denoting nutrition element classes may relate to magnitudes, such as nutrient effect and/or serving size, which are graphed along the circle corresponding to the frequency, or timeline on which they are expected to be consumed. User may indicate which nutrition element from each category was consumed and when it was consumed, to arrive at an, for instance as adherence score, which increases as user participates and decreases as they fall short of nutrient amounts.

Figure 6:
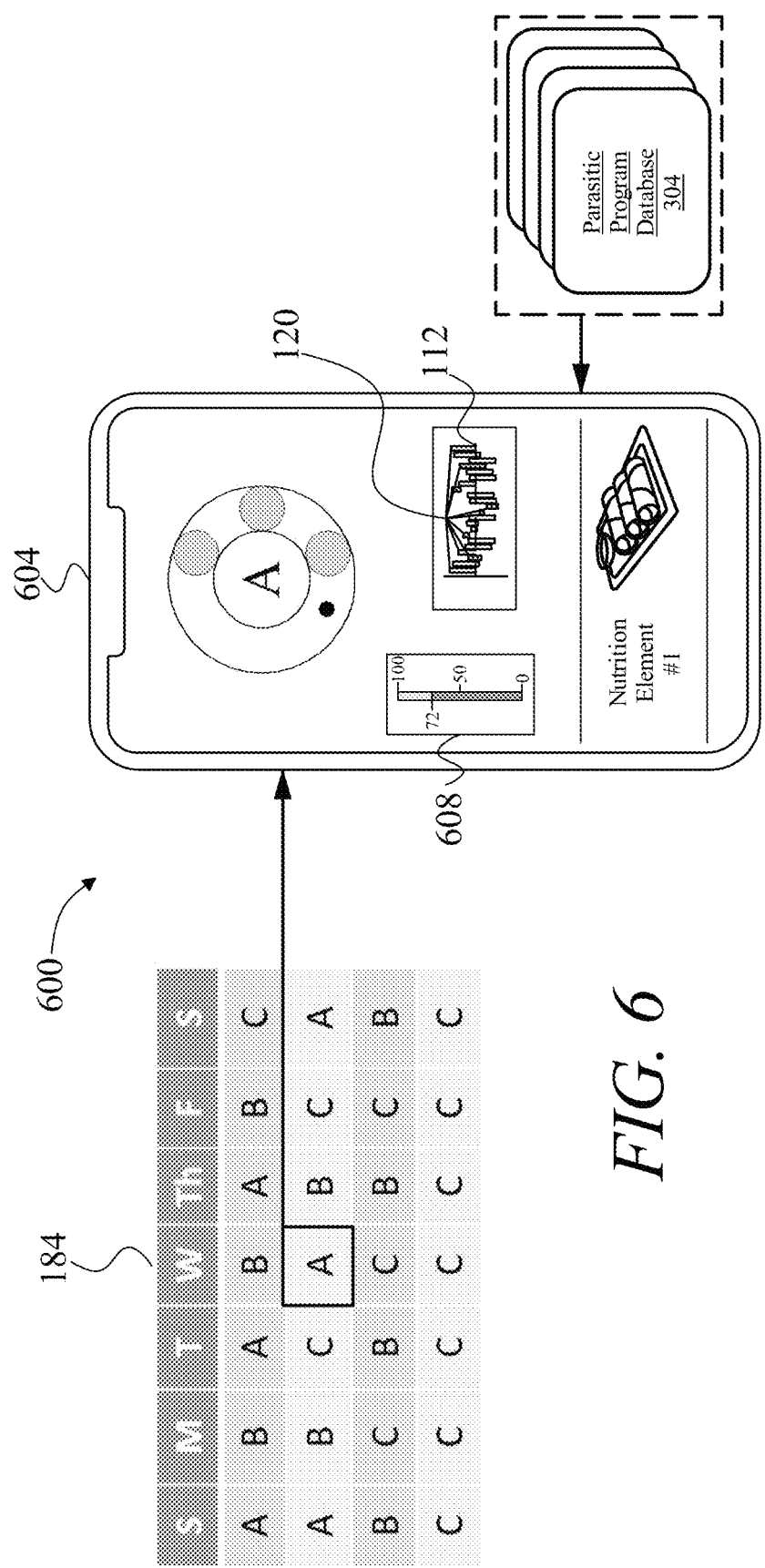
FIG. 6 is a diagrammatic representation of a user device.

Referring now to FIG. 6, a non-limiting exemplary embodiment 600 of a user device 604 is illustrated. User device 604 may include computing device 104, a "smartphone," cellular mobile phone, desktop computer, laptop, tablet computer, internet-of-things (IOT) device, wearable device, among other devices. User device 604 may include any device that is capable for communicating with computing device 104, parasitic program database 304, or able to receive, transmit, and/or display, via a graphical user interface, parasitic background 112, nutrition elements, parasitic infection nutrition program 184, among other outputs from system 100. User device 604 may provide an "adherence score," which as used in this disclosure, is a metric that enumerates a user's overall parasitic disease state according to adherence to parasitic infection nutrition program 184. Adherence score 608 may increase and/or decrease with varying levels of participation and/or adherence to parasitic infection nutrition program 184. For instance, the starting adherence score 608 may be related to the current position 128 parasitic infection rate, the user's current parasitic background. In such an instance, the adherence score 608 may increase as the user meets daily nutrient amounts, as indicated by ordering nutrition elements provided via parasitic infection nutrition program 184. Likewise, adherence score 608 may decrease as user falls chronically short of nutrient amounts. Adherence score 608 may be generated as a function of generating an adherence model, for instance using a machine-learning algorithm, process, and/or model, as performed by machine-learning module 200. Training data for adherence score 608 may include a plurality of data entries of nutrient amounts correlated to effect on parasitic infection and prevention. Such an adherence model may determine a scoring function which derives an upper limit, lower limit, and scoring criteria for increasing/decreasing score.

Still referring to FIG. 6, user device 604 may provide a parasitic background 112, for instance as a collection of parameters determined from parasitic biomarker 108 data. User device 604 may provide parasitic disease assessment 120 that was determined as a function of parasitic background 112. User device 604 may provide data concerning nutrient amounts, including the levels of specific nutrients, nutrient ranges, nutrients to avoid, and the like User device 604 may link timing of foods to preemptive ordering interface for ordering a nutrition element, for instance and without limitation, through a designated mobile application, mapping tool or application, and the like, and a radial search method about a user's current position 128 as described in U.S. Nonprovisional application Ser. No. 17/087,745, filed Nov. 3, 2020, titled "A METHOD FOR AND SYSTEM FOR PREDICTING ALIMENTARY ELEMENT ORDERING BASED ON BIOLOGICAL EXTRACTION," the entirety of which is incorporated herein by reference. User device 604 may display nutrition elements as a function of current position 128 and/or geophysical indicator 160. User device 604 may link parasitic infection nutrition program 184 to a scheduling application, such as a 'calendar' feature on user device 604, which may set audio-visual notifications, timers, alarms, and the like.

Continuing in reference to FIG. 6, user device 604 may include any device that is capable for communicating with computing device 104, database, or able to receive data, retrieve data, store data, and/or transmit data, for instance via a data network technology such as 3G, 4G/LTE, 5G, Wi-Fi (IEEE 802.11 family standards), and the like. User device may include devices that communicate using other mobile communication technologies, or any combination thereof, for short-range wireless communication (for instance, using Bluetooth and/or Bluetooth LE standards, AirDrop, Wi-Fi, NFC, and the like), and the like.

Figure 7:
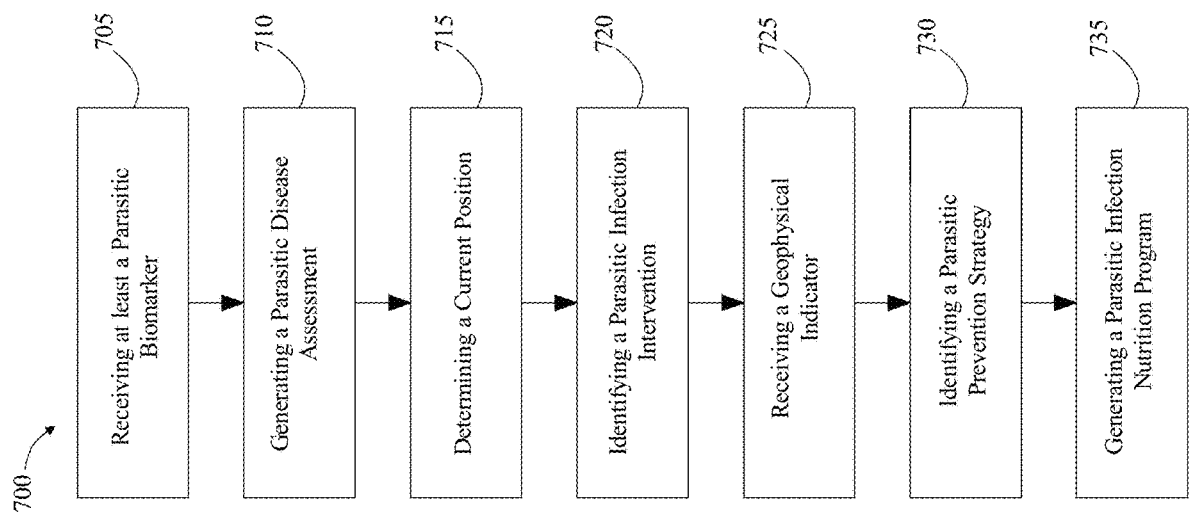
FIG. 7 is a block diagram of a work flow of a method for generating a parasitic infection nutrition program.

Referring now to FIG. 7, an exemplary embodiment 700 of a method for generating a parasitic infection nutrition program 184 is illustrated. At step 705, the method includes receiving, by a computing device 104, at least a parasitic biomarker 108; this may be implemented, without limitation, as described above in FIGS. 1-6.

Still referring to FIG. 7, at step 710, method includes generating, by the computing device 104, a parasitic disease assessment 120 as a function of the at least a parasitic biomarker 108. Generating the parasitic disease assessment 120 may include generating a parasitic background 112, wherein generating the parasitic background 112 includes generating parasitic background training data using the at least a parasitic biomarker 108, training a parasitic background machine-learning model 116 with the parasitic background training data that includes a plurality of data entries wherein each entry correlates parasitic biomarkers to a plurality of parasitic diseases, and generating the parasitic background 112 as a function of the parasitic background machine-learning model 116 and the at least a parasitic biomarker 108. Generating the parasitic disease assessment 120 may include assigning the parasitic background 112 to the parasitic disease assessment 120, wherein assigning the parasitic background 112 includes classifying the parasitic background 112 to the parasitic disease assessment 120 using an assessment classification machine-learning process 124 and assigning the parasitic background 112 as a function of the classifying; this may be implemented, without limitation, as described above in FIGS. 1-6.

Continuing in reference to FIG. 7, at step 715, method includes determining, by the computing device 104, a current position 128 of the user; this may be implemented, without limitation, as described above in FIGS. 1-6.

Continuing in reference to FIG. 1, at step 720, method includes identifying, by the computing device 104, using the current position 128 and the parasitic disease assessment 120, a parasitic infection intervention 132. Identifying the parasitic infection intervention 132 may include calculating a parasitic infection rate, wherein calculating the parasitic infection rate includes training an infection rate model 140 using an intervention machine-learning process and training data, wherein training data includes a plurality of data entries of parasitic disease correlated to a plurality of locations, and calculating the first parasitic infection rate as a function of the current position 128 and the infection rate model 140. Identifying the parasitic infection intervention 132 may include determining at least a first nutrient amount 144, wherein determining the at least a first nutrient amount 144 includes training a parasitic infection intervention model 148 using an infection machine-learning process and training data, wherein training data includes a plurality of data entries of nutrition amounts correlated to addressing parasitic infection, and determining the at least a first nutrient amount 144 as a function of at least the parasitic disease assessment 120 and the parasitic infection intervention model 148. Determining the at least a first nutrition element 152 may include training a nutrition model 156 using a nutrition machine-learning process and training data, wherein training data includes a plurality of data entries of nutrition amounts correlated to nutrition elements and identifying the at least a first nutrition element as a function of the at least a first nutrient amount and the nutrition model 156; this may be implemented, without limitation, as described above in FIGS. 1-6.

Continuing in reference to FIG. 7, at step 725, method includes receiving, by the computing device 104, a geophysical indicator 160 relating to the user; this may be implemented, without limitation, as described above in FIGS. 1-6.

Continuing in reference to FIG. 7, at step 730, method includes identifying, by the computing device 104, using the geophysical indicator 160, a parasitic prevention strategy 164 regarding a second parasitic infection. Identifying the parasitic prevention strategy 164 may include comparing the parasitic infection rate of the current position 128 with a second parasitic infection rate of the geophysical indicator 160, wherein comparing may include calculating a difference in parasitic infection rate as a function of difference in location between the current position 128 and the geophysical indicator 160. Identifying the parasitic prevention strategy 164 may include determining at least a second nutrient amount, wherein determining the at least a second nutrient amount includes training a parasitic prevention model 176 using a prevention machine-learning process and training data, wherein training data includes a plurality of data entries of regional nutrition elements correlated to preventing parasitic infection, and determining the at least a second nutrient amount as a function of at least the geophysical indicator 160 and the parasitic prevention model 176; this may be implemented, without limitation, as described above in FIGS. 1-6.

Continuing in reference to FIG. 7, at step 735, method includes generating, by the computing device 104, a parasitic infection nutrition program 184, using the parasitic infection intervention 132 and the parasitic prevention strategy 164. The parasitic infection nutrition program 184 may include a frequency and a magnitude of the parasitic infection intervention 132 and a frequency and a magnitude of the parasitic prevention strategy 164. Generating the parasitic infection nutrition program 184 may include generating an objective function with the parasitic infection intervention 132 and the parasitic prevention strategy 164, wherein the objection function outputs at least an ordering of a plurality of nutrition elements according to constraints of the current position 128 and the geophysical indicator 160; this may be implemented, without limitation, as described above in FIGS. 1-6.

It is to be noted that any one or more of the aspects and embodiments described herein may be conveniently implemented using one or more machines (e.g., one or more computing devices that are utilized as a user computing device for an electronic document, one or more server devices, such as a document server, and the like) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, and the like), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, and the like), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
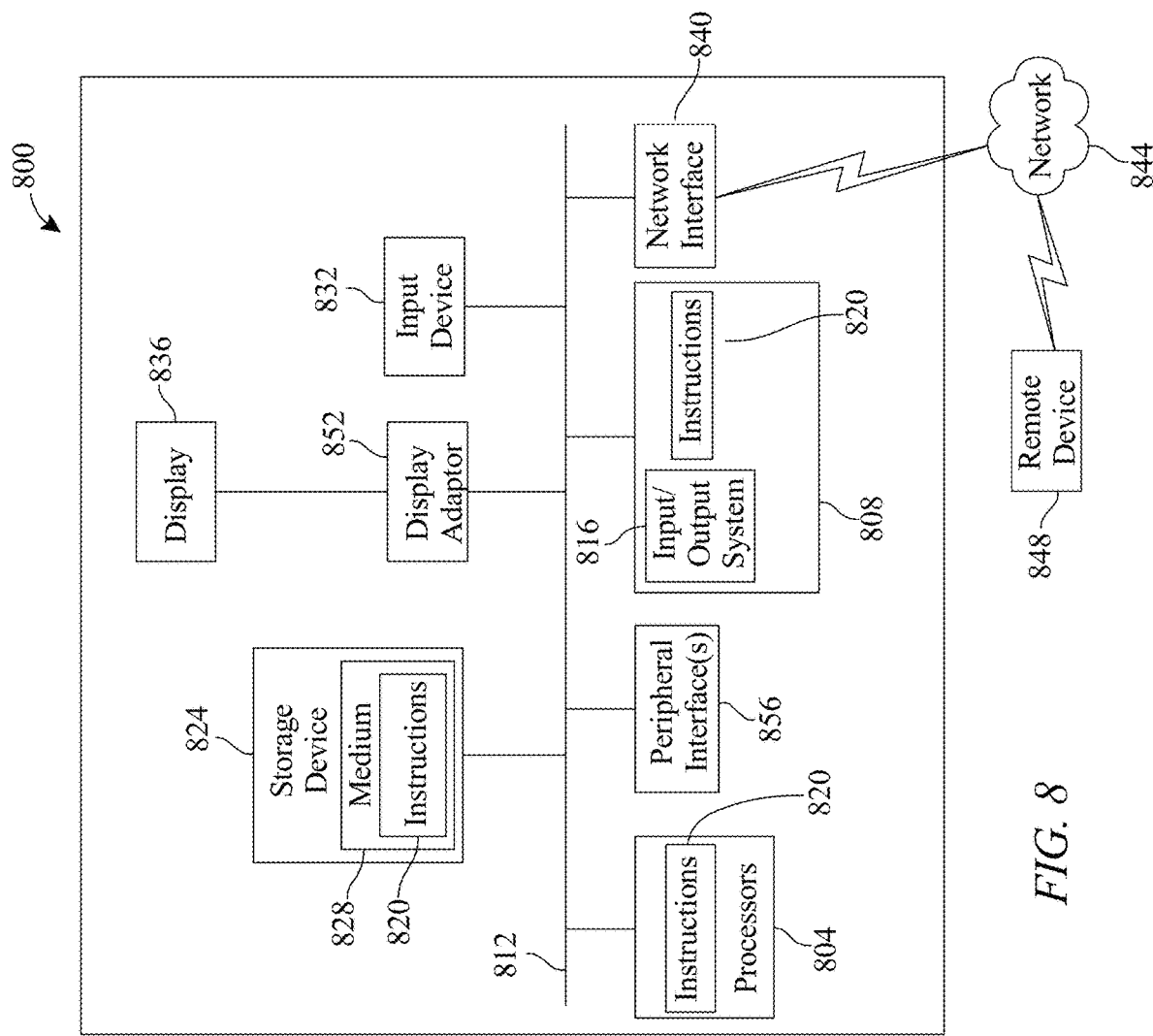
FIG. 8 is a block diagram of a computing system that can be used to implement any one or more of the methodologies disclosed herein and any one or more portions thereof.

Referring now to FIG. 8, a diagrammatic representation of one embodiment of a computing device in the exemplary form of a computer system 800 within which a set of instructions for causing a control system to perform any one or more of the aspects and/or methodologies of the present disclosure may be executed is illustrated. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Continuing in reference to FIG. 8, processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Continuing in reference to FIG. 8, memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Continuing in reference to FIG. 8, computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Continuing in reference to FIG. 8, computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, and the like), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

Continuing in reference to FIG. 8, a user may also input commands and/or other information to computer system 800 via storage device 824 (e.g., a removable disk drive, a flash drive, and the like) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, and the like) may be communicated to and/or from computer system 800 via network interface device 840.

Continuing in reference to FIG. 8, computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a parasitic infection nutrition program, the system comprising:
    a computing device, wherein the computing device is configured to:
    receive a parasitic background training data, the training data using, at least a parasitic biomarker, parasitic biomarker including at least a host factor;
    train a parasitic background machine-learning model with the parasitic background training data, parasitic background training data including a plurality of data entries wherein each entry correlates parasitic biomarkers to a plurality of parasitic disease;
    generate a parasitic disease assessment referring to a first parasitic infection as a function of the parasitic background machine-learning model, wherein the machine learning model uses the at least a parasitic biomarker as an input and outputs the parasitic disease assessment;
    determine a current position of a user;
    determine an infection risk threshold for the user as a function of the current position of the user;
    identify, using the determination of the infection risk threshold for the user and the parasitic disease assessment, a parasitic infection intervention;
    receive a geophysical indicator relating to the user;
    identify, using the geophysical indicator a parasitic prevention strategy regarding a second parasitic infection; and
    generate a parasitic infection nutrition program, using machine-learning to calculate nutrient amounts and nutrition elements as a function of changes in parasitic infection rates and regional nutrition elements, and using the parasitic infection intervention and the parasitic prevention strategy;
    link the parasitic infection nutrition program to a scheduling application of a user device of the user; and
    display, through the user device, the nutrient amounts and nutrition elements of the parasitic infection nutrition program.

2. The system of claim 1, wherein generating the parasitic disease assessment further comprises assigning the parasitic background to the parasitic disease assessment, wherein assigning the parasitic background includes:
    classifying the parasitic background to the parasitic disease assessment using an assessment classification machine-learning process; and
    assigning the parasitic background as a function of the classifying.

3. The system of claim 1, wherein identifying the parasitic infection intervention further comprises calculating a parasitic infection rate, wherein calculating the parasitic infection rate includes:
    training an infection rate model using an intervention machine-learning process and training data, wherein training data includes a plurality of data entries of parasitic disease correlated to a plurality of locations; and
    calculating the first parasitic infection rate as a function of the current position and the infection rate model.

4. The system of claim 1, wherein identifying the parasitic infection intervention further comprises determining at least a first nutrient amount, wherein determining the at least a first nutrient amount includes:
    training a parasitic infection intervention model using an infection machine-learning process and training data, wherein training data includes a plurality of data entries of nutrition amounts correlated to addressing parasitic infection; and determining the at least a first nutrient amount as a function of at least the parasitic disease assessment and the parasitic infection intervention model.

5. The system of claim 4, wherein determining the at least a first nutrition element further comprises:

training a nutrition model using a nutrition machine-learning process and training data, wherein training data includes a plurality of data entries of nutrition amounts correlated to nutrition elements; and identifying the at least a first nutrition element as a function of the at least a first nutrient amount and the nutrition model.

6. The system of claim 1, wherein identifying the parasitic prevention strategy further comprises comparing the parasitic infection rate of the current position with a second parasitic infection rate of the geophysical indicator, wherein comparing further comprises calculating a difference in parasitic infection rate as a function of difference in location between the current position and the geophysical indicator.

7. The system of claim 1, wherein identifying the parasitic prevention strategy further comprises determining at least a second nutrient amount, wherein determining the at least a second nutrient amount includes:

training a parasitic prevention model using a prevention machine-learning process and training data, wherein training data includes a plurality of data entries of regional nutrition elements correlated to preventing parasitic infection; and determining the at least a second nutrient amount as a function of at least the geophysical indicator and the parasitic prevention model.

8. The system of claim 1, wherein the parasitic infection nutrition program further comprises a frequency and a magnitude of the parasitic infection intervention and a frequency and a magnitude of the parasitic prevention strategy.

9. The system of claim 1, wherein generating the parasitic infection nutrition program further comprises generating an objective function with the parasitic infection intervention and the parasitic prevention strategy, wherein the objection function outputs at least an ordering of a plurality of nutrition elements according to constraints of the current position and the geophysical indicator.

10. The system of claim 1, wherein the regional nutrition element includes a dairy product.

11. The system of claim 1, wherein generating the parasitic infection nutrition program comprises using regional water sources.

12. A method for generating a parasitic infection nutrition program, the method comprising:

receiving, by a computing device, a parasitic background training data, the training data using, at least a parasitic biomarker, parasitic biomarker including at least a host factor;

training a parasitic background machine-learning model with the parasitic background training data, parasitic background training data including a plurality of data entries wherein each entry correlates parasitic biomarkers to a plurality of parasitic disease; and generating, by the computing device, a parasitic disease assessment referring to a first parasitic infection as a function of the parasitic background machine-learning model, wherein the machine learning model uses the at least a parasitic biomarker as an input and the parasitic disease assessment as the at least an output;

determining, by the computing device, a current position of a user;

determine an infection risk threshold for the user as a function of the current position;

identifying, by the computing device, using the determination of the infection risk threshold for the user and the parasitic disease assessment, a parasitic infection intervention;

receiving, by the computing device, a geophysical indicator relating to the user;

identifying, by the computing device, using the geophysical indicator, a parasitic prevention strategy regarding a second parasitic infection;

generating, by the computing device, a parasitic infection nutrition program, using machine-learning to calculate nutrient amounts and nutrition elements as a function of changes in parasitic infection rates and regional nutrition elements and using the parasitic infection intervention and the parasitic prevention strategy;

linking, by the computing device, the parasitic infection nutrition program to a scheduling application of a user device of the user; and displaying, through the user device, the nutrient amounts and nutrition elements of the parasitic infection nutrition program.

13. The method of claim 12, wherein generating the parasitic disease assessment further comprises assigning the parasitic background to the parasitic disease assessment, wherein assigning the parasitic background includes:

classifying the parasitic background to the parasitic disease assessment using an assessment classification machine-learning process; and assigning the parasitic background as a function of the classifying.

14. The method of claim 12, wherein identifying the parasitic infection intervention further comprises calculating a parasitic infection rate, wherein calculating the parasitic infection rate includes:

training an infection rate model using an intervention machine-learning process and training data, wherein training data includes a plurality of data entries of parasitic disease correlated to a plurality of locations; and calculating the first parasitic infection rate as a function of the current position and the infection rate model.

15. The method of claim 12, wherein identifying the parasitic infection intervention further comprises determining at least a first nutrient amount, wherein determining the at least a first nutrient amount includes:

training a parasitic infection intervention model using an infection machine-learning process and training data, wherein training data includes a plurality of data entries of nutrition amounts correlated to addressing parasitic infection; and determining the at least a first nutrient amount as a function of at least the parasitic disease assessment and the parasitic infection intervention model.

16. The method of claim 15, wherein determining the at least a first nutrition element further comprises:

training a nutrition model using a nutrition machine-learning process and training data, wherein training data includes a plurality of data entries of nutrition amounts correlated to nutrition elements; and identifying the at least a first nutrition element as a function of the at least a first nutrient amount and the nutrition model.

17. The method of claim 12, wherein identifying the parasitic prevention strategy further comprises comparing the parasitic infection rate of the current position with a second parasitic infection rate of the geophysical indicator, wherein comparing further comprises calculating a difference in parasitic infection rate as a function of difference in location between the current position and the geophysical indicator.

18. The method of claim 12, wherein identifying the parasitic prevention strategy further comprises determining at least a second nutrient amount, wherein determining the at least a second nutrient amount includes:

training a parasitic prevention model using a prevention machine-learning process and training data, wherein training data includes a plurality of data entries of regional nutrition elements correlated to preventing parasitic infection; and determining the at least a second nutrient amount as a function of at least the geophysical indicator and the parasitic prevention model.

19. The method of claim 12, wherein the parasitic infection nutrition program further comprises a frequency and a magnitude of the parasitic infection intervention and a frequency and a magnitude of the parasitic prevention strategy.

20. The method of claim 12, wherein generating the parasitic infection nutrition program further comprises generating an objective function with the parasitic infection intervention and the parasitic prevention strategy, wherein the objection function outputs at least an ordering of a plurality of nutrition elements according to constraints of the current position and the geophysical indicator.

* * * * *